United States Patent [19] [11] 4,020,158
Ashmead et al. [45] Apr. 26, 1977

[54] INCREASING METALS IN BIOLOGICAL TISSUE

[76] Inventors: Harvey H. Ashmead, 719 E. Center St., Kaysville, Utah 84037; Paul A. Little, P.O. Box 172, Avivaca, Ariz. 85601

[22] Filed: Feb. 17, 1976

[21] Appl. No.: 658,243

Related U.S. Application Data

[63] Continuation-in-part of Ser. No. 607,370, Aug. 8, 1975, abandoned, which is a continuation-in-part of Ser. No. 420,033, Nov. 29, 1973, abandoned, which is a continuation-in-part of Ser. No. 739,141, June 24, 1968, abandoned.

[52] U.S. Cl. .............................. 424/177; 424/287; 424/289; 424/294; 424/295; 424/319
[51] Int. Cl.$^2$ ............... A61K 37/00; A61K 31/295
[58] Field of Search .......... 424/177, 287, 289, 294, 424/295, 319

[56] References Cited

UNITED STATES PATENTS

| | | | |
|---|---|---|---|
| 1,824,018 | 9/1931 | Horn | 424/177 |
| 2,481,413 | 9/1949 | Grindrod | 424/177 |
| 2,960,406 | 11/1960 | Cardon | 426/2 |
| 2,982,690 | 5/1961 | Ratcliff | 424/295 |
| 3,168,541 | 2/1965 | Hobbs | 260/439 |
| 3,374,081 | 3/1968 | Miller | 71/11 |
| 3,396,104 | 8/1968 | Miller | 210/54 |
| 3,463,858 | 8/1969 | Anderson | 424/289 |
| 3,911,117 | 10/1975 | Ender | 462/2 |

Primary Examiner—Leonard Schenkman
Attorney, Agent, or Firm—Criddle, Thorpe & Western

[57] ABSTRACT

The levels of nutritionally essential metals in biological tissue are improved by administering corrective dosages of the metals found to be deficient, the metal being administered in the form of metal proteinates. General health of animals is improved by increasing the levels of metals in biological tissues through the administration of multiple metals in the form of metal proteinates.

14 Claims, No Drawings

INCREASING METALS IN BIOLOGICAL TISSUE

BACKGROUND OF THE INVENTION

1. Field of the Invention

This is a continuation-in-part of our copending U.S. patent application Ser. No. 607,370, filed Aug. 8, 1975, now abandoned which in turn is a continuation-in-part of Ser. No. 420,033, filed Nov. 29, 1973, now abandoned which in turn was a continuation-in-part of U.S. patent application Ser. No. 739,141, filed June 24, 1968, now abandoned.

The present invention relates to the preparation and administration of dietary metal proteinate supplements designed to increase metal levels and correct metal deficiencies in animal tissues.

2. The Prior Art

It is well known that certain metals are essential to the growth and well being of animals. These metals are present in the biological tissue of the animal and, although some are present in only trace amounts, contribute significantly to the metabolic processes.

Recent studies of the levels of bivalent metals in solution in different biological cells have indicated that metal concentration gradients in the cells correlate with the general health of an animal and its resistance to certain diseases. It has been found that examination of the metal content of skin, feathers and other animal tissues from various locations may serve as an indicator as to dietary deficiencies or inadequate metal metabolism adversely affecting the metal intake of the animal.

The present invention provides an improved method for increasing the uptake of essential bivalent metals into animal tissues and diagnosing and treating metal deficiencies in animals by analyzing skin, feathers, hair, and/or other tissue from selected animals and comparing the metal content and distribution found therein with values obtained from similar tissue specimens derived from healthy and productive control animals. Assay results from the healthy, productive animals are then used as a basis for formulating an effective dietary supplement composition for treating animals diagnosed as having metal deficiencies. The needed metals are then incorporated into a feed supplement in a chelated form readily assimilable by the animal.

Historically, it has been customary to amend the dietary intake of the animal with inorganic forms of the desired metals to correct deficiencies in the levels of these metals. However, the inorganic form of these metals have not been found to be assimilated easily by the animal. In certain instances, large dosages of the inorganic form of some metals designed to achieve the desired metal level in the tissue may be toxic to the ingesting animal.

It would, therefore, be a significant contribution to the art to provide a procedure whereby the biological tissue was assayed to determine metal deficiencies, if any, and the diet of the animal was amended with a corrective supplement including metals in readily assimilable form to overcome the deficiency.

Certain prior art patents have attempted to alleviate certain metal deficiencies by the utilization of organometallic preparations. For example, U.S. Pat. No. 1,824,018 teaches combinations of iron and copper compounds for the treatment of anemia. As related to the present invention, the example showing the combination of copper caseinate and iron peptonate is perhaps most pertinent. Copper caseinate is a combination of copper with casein which has not been hydrolyzed and which may be defined as an insoluble protein salt. This product may be described as the interaction of a metallic copper with an intact protein, but does not produce a metal proteinate or chelate as hereinafter described. Likewise, this patent discloses an iron peptonate. Iron peptonate is described in the National Formulary V as a compound of iron oxide and peptone rendered soluble by the presence of sodium citrate. Again, this is not a metal proteinate or chelate as will be described.

U.S. Pat. No. 505,986 describes an iron albumen preparation which is a combination of an unhydrolyzed protein which has been heat coagulated. The iron present attaches itself to the surface of the protein molecule and a precipitate is formed. According to the patent this product is readily soluble in a weakly alkaline solution. It cannot therefore be considered to be a metal chelate formed from a protein hydrolysate for such a product would be insoluble in basic solution.

U.S. Pat. No. 2,481,413 teaches the preparation of metal caseinates which again are salts or compounds of a protein molecule with metal ions attached thereto, but are not metal chelates.

A more recently issued patent, U.S. Pat. No. 2,960,406 teaches soluble trace metals which are allegedly chelated, preferably using EDTA as a chelating agent. According to that patent, when any of the described metal salts are introduced into water, metal chelates will form in the water solution. While EDTA and its salts are strong chelating agents, naturally occurring amino acids, peptides and polypeptides will not form a chelate merely by their combination with a soluble metal salt in water. Therefore, while U.S. Pat. No. 2,960,406 may teach chelates with EDTA and its derivatives, there are insufficient data in the patent to teach the preparation of metal proteinates. The mere combination of a metal salt and a naturally occurring amino acid or protein hydrolysate in an aqueous solution is insufficient for reasons later hereinafter described.

Additionally, U.S. Pat. No. 3,463,858 teaches a process of making a feed additive by slurrying a mixture containing an amino acid source and a water soluble zinc salt, heating, acidifying and drying the slurry. Since this patent teaches that the optimum pH for combining zinc with amino acids is about 3.5, this is inimical to chelate formation.

BRIEF DESCRIPTION AND OBJECTS OF THE INVENTION

The present invention provides a unique system for making nutritionally essential bivalent metals abundantly available to biological tissue in the form of exogenously synthesized metabolically assimilable metal chelates. In some circumstances, it has been found desirable to first determine metal deficiency by tissue analysis.

It is, therefore, a primary object of the present invention to provide improvements in the art of increasing the levels of essential bivalent metals in biological tissues.

It is another object of the present invention to provide an exogenously synthesized dietary supplement for increasing levels of essential bivalent metals in biological tissues.

It is still another object of this invention to provide a readily assimilable bivalent metal dietary supplement wherein the metal is present in the form of a chelate with at least one of a group comprising a protein hydrolysate which is a polypeptide, peptide, amino acid or mixture of the same.

It is an even still further object of this invention to provide a procedure whereby metal deficiencies in biological tissues are first ascertained and the deficiencies then corrected.

These and other objects and features of the present invention will become more fully apparent from the following description and appended claims.

DETAILED DESCRIPTION OF THE PREFERRED EMBODIMENTS

In General

This correction of dietary deficiencies as they relate to nutritionally essential bivalent metals such as calcium, magnesium, zinc, iron, manganese, copper and cobalt requires a knowledge of the existing levels of these metals in the biological tissue in comparison with the nutritionally desirable levels of those metals, the latter serving as a standard. Once these levels are known, it is possible to amend the diet of the animal with the required metals in a form readily assimilable by the animal to bring the existing metals level up to the standard. It has been found that a chelate of the metal with a protein hydrolysate or naturally occurring amino acid renders the metal more readily assimilable than if the metal were in an inorganic form or in a different organic form.

Metal proteinates are defined at page 89 of the *Official Publication of the American Feed Control Officials, Inc.* as "the product resulting from the chelation of a soluble salt with amino acids and/or partially hydrolyzed protein". That definition is hereby incorporated in this specification. Metal proteinates are readily commercially available (see U.S. Pat. Nos. 3,440,054, 3,374,081 and 3,396,104).

Protein hydrolysates are prepared in either acidic or basic media. It is beneficial to first hydrolyze a protein source well so that the subsequent formation of the metal proteinate or chelate can form a product that can be actively transported through the walls of the small intestine. Large protein entities such as metal salts of gelatinates, caseinates or albuminates must be digested before transport can take place. It is believed that unhydrolyzed protein salts, in general, pass through the intestine largely intact with only small amounts being utilized. Therefore, in the present invention the protein molecules are hydrolyzed to a polypeptide, peptide or amino acid stage prior to mixing with the metal salt to form a proteinate (chelate with a protein hydrolysate as the ligand). In order to form a metal proteinate the proper amounts of constituents must be present at the right conditions. The mineral to be chelated must be in soluble form and the protein hydrolysates or amino acids must be free from interfering protons, i.e. non-intact, in the chelation process so that chemical bonds can be formed between the proteinate ligand and the metal involved. Since chelates, by definition, are molecular structures in which a heterocyclic ring can be formed by the unshared electrons of neighboring atoms, it is essential that before a protein hydrolysate can complex with a metal ion to form cordinate bonds, that the protons in the chelating agent, i.e., the amino acid or protein hydrolysate be removed. Again, by definition, a chelating agent is considered to be an organic compound in which molecules form more than one cordinate bonds with metals in solution. Thus it is essential that the chelation process take place in solution. Once the chelating mineral salt is completely soluble and the protein hydrolysates are completely soluble, the pH must be adjusted to a point that is sufficiently basic to remove interfering protons from both the amine groups and the carboxyl groups. While a pH of 7.5 may be sufficient a pH in the range of 8–10 is preferred. This allows the heterocyclic rings to form from covalent bonds between the positive mineral ions and the lone pairs of electrons left behind on the carboxyl and amine groups. Thus, the mere mixing of intact amino acids or intact protein hydrolysates with water in the presence of a metal salt will not result in a chelate or proteinate because the protons on the carboxyl and amine groups interfere with chelate formation. When combining protonated or intact proteins or protein hydrolysates with a soluble metal salt either no reaction takes place or a salt may be formed from the metal with the protein or protein hydrolysate, which salt may be soluble or may precipitate. The metal proteinates formed as described precipitate in basic solutions and are insoluble or only partially soluble in water solutions. Moreover, metal proteinates or chelates are heterocyclic complexes and are vastly different from metal salts of proteins or amino acids. The metal proteinates more readily assimilated and ingested through the small intestine making the metal more readily available to the body tissues.

While it is possible to form metal chelates with many different ligands it has been found that metal proteinates are vastly superior in being metabolically assimilated into the body. Other chelates such as chelates with EDTA (ethylenediaminetetraaceticacid) form such strong complexes that the metal is not readily assimilated by the body and may, in fact, not be available to the body at all. Chelates formed from other ligands such as ascorbic or citric acids are not as beneficial since proteinates are more readily assimilated or utilized by the body.

Historically, trial and error has been employed in the selection of the products found to be the most effective in the particular diet and for the correction of dietary deficiencies. This means that excessive quantities of certain metals may be administered to the animal during the trial period and, since it was trial and error, only one metal could be tested at a time to assure accuracy of results.

According to the present invention, animal tissue, for example hair, is assayed and then the diet amended with the correct dietary supplement having a plurality of metal chelates, if necessary, without resorting to the time consuming and perhaps even risky trial and error method for correcting dietary deficiencies. This system is preferable over one that employs a broad spectrum dietary supplement to all animals since, ideally, only those metals which are deficient should be administered and then only in the amounts required to correct the deficiency. The correction is advantageously applied with a plurality of metals versus the application of one metal at a time.

Analysis of tissue such as hair permits one to obtain an average metals level value measured over several days or weeks since the hair retains the metal level acquired during its growth and thus reflects the metal profile of the animal over an extended period of time. These values are more valuable as compared to a direct muscle tissue sample, for example, which may reflect the recent diet only without reflecting the overall metal profile of the animal tissues. Feathers have also been found useful as a tool for determining average metal values.

Optimal proportions of the different essential metals are prepared such that they appropriately correct deficiencies in the animal or bird as determined by analysis of the metals found in the hair and feathers of metals deficient animals and birds. The standard against which the foregoing deficiency is measured is that of the proportions of metals found in the hair and feathers of healthy animals and birds. The latter is a more realistic guide to formulation than to base the formulation on theoretical minimal requirements since the idiosyncrasies of the individual breed of animal or bird are taken into consideration.

To further prove the efficacy of the present invention, particularly as it relates to raising metal levels in biological tissues, the following examples and tables list representative comparisons of metal levels in biological tissues from treated animals (diet supplemented with metal proteinates) as compared to a control group of animals (diet supplemented with corresponding amounts of inorganic forms of metals).

EXAMPLE I

Into 16 pounds of water was added 5.7 pounds of concentrated hydrochloric acid. To this acid solution was added 10 pounds of soy protein. The mixture was heated to 130° C and maintained for 4 hours to form a protein hydrolysate. The hydrolysate was neutralized with 4 pounds of zinc carbonate and the pH as adjusted to 8.5 by the addition of about 1.1 pounds of sodium hydroxide. A zinc proteinate (chelate) was formed as a precipitate which was filtered, washed and dried, to produce about 10 pounds of proteinate. Upon analysis of the proteinate was found to contain about 17% of weight zinc.

The above procedure can be repeated using phosphoric or sulfuric acids in the place of hydrochloric acid. Any suitable protein source can be used. In the place of zinc carbonate any bivalent metal salt which is soluble in the aqueous solution can be used. Typical salts include ferrous sulfate ferric chloride, cupric chloride, manganese chloride, magnesium sulfate, and the like.

EXAMPLE 2

In this series of experiments, day-old chicks were divided into groups and each group, control and treated, was fed the same commercial chick-starter ration. For example, one commercial chick-starter ration has the following composition: soy bean meal, meat meal, ground corn, ground milo, salt, fat, dicalcium carbonate, limestone, and an inorganic trace mineral mix. This chick-starter ration had 22% protein, and a fat content giving a metabolizable caloric content of 1250 calories per pound. The ration also contained vitamins in addition to the standard inoganic mineral supplement. Each group of chicks referred to as "treated" received a different predetermined quantity of metal proteinate (as set forth in the following tables) in addition to the above commercial chick-starter ration. Chicks fed the commercial chick-starter ration plus corresponding amounts of inorganic metals served as the control.

The comparison results are reported as a T/C ratio to indicate the concentration of metal in treated chicks as compared to the concentration of metal in control chicks. Accordingly, a T/C ratio greater than one indicates that there is a greater concentration of metal in the tissue of the treated chick as compared to the concentration of metal in a similar sample of tissue from the control chick. A T/C ratio less than one indicates the reverse.

One purpose of the comparison was to demonstrate the increase in metals assimilation by chicks which were fed metal proteinates as compared to chicks fed inorganic metals.

Table I reflects the T/C ratio for treated and control chicks in various tissues 10 days after treatment commenced.

TABLE I

| | EFFECT OF METAL PROTEINATE IN CHICK RATION AFTER 10 DAYS (Reported as T/C Ratio) | | | | |
|---|---|---|---|---|---|
| Tissue | 2% Zinc Proteinate | 2% Magnesium Proteinate | 2% Calcium Proteinate | 0.5% Manganese Proteinate | 0.5% Cobalt Proteinate |
| Brain | 1.43 | 1.35 | 0.48 | None | None |
| Heart | 1.36 | 0.92 | 1.00 | Raised to Detectable Level | Raise to Detectable Level |
| Liver | 25.77 | 1.41 | 1.00 | 0.5 | Raised to Detectable Level |
| Breast | 2.17 | 1.20 | 1.09 | None | None |
| Skin | 2.32 | 1.60 | 1.62 | Lowered | Raised to Detectable Level |
| Whole Leg | 5.46 | 1.31 | 8.69 | 1.00 | Raised to Detectable Level |

EXAMPLE 3

The beneficial stimulation of growth by the addition of metal proteinates to the diet of turkey poults was also determined.

Turkey poult hens (1- day old) were divided into five groups and each group was placed on a commercially available pre-starter ration. The first group served as the control and received no supplementary metals. The remaining four groups were treated as follows:

Group 2: Given a (1X) capsule (see Table II)daily by mouth.

Group 3: Given a (0.1X) capsule (see Table II) daily by mouth.

Group 4: Given a (0.01X) capsule (see Table II) daily by mouth.

Group 5: Given 0.01X level of metal proteinate blend in the pre-starter ration which was prepared by mixing 10 grams of (1X) metal proteinate blend with 990 grams of pre-starter ration.

The metals dosage per capsule is also given in Table II. Dilution of the starting amount (1X) was made in factors of ten (0.1X) and (0.01X) with lactose diluent.

TABLE II

| Metal | METAL DOSAGE PER CAPSULE | | |
|---|---|---|---|
| | (1×) mg/capsule | (0.1×) mg/capsule | (0.01×) mg/capsule |
| Co | 0.0296 | 0.00296 | 0.000296 |
| Cu | 0.0459 | 0.00459 | 0.000459 |
| Mn | 0.115 | 0.0115 | 0.00115 |
| Fe | 0.230 | 0.0230 | 0.00230 |
| Zn | 0.492 | 0.0492 | 0.00492 |
| Ca | 4.592 | 0.459 | 0.0459 |
| Mg | 4.592 | 0.459 | 0.0459 |

The average daily weights for each group was then determined and is reported in Table III.

TABLE III

AVERAGE DAILY WEIGHTS OF TURKEY POULTS
(All Weights in Grams)

| | 1st Day | 2nd Day | 3rd Day | 4th Day | 5th Day |
|---|---|---|---|---|---|
| Group 1 (Control) | 48.7 | 51.4 | 60.0 | 64.3 | 74.6 |
| Group 2 (1 × Capsule) | 50.7 | 50.5 | 65.8 | 73.4 | 80.9 |
| Group 3 (0.1 × Capsule) | 50.6 | 53.4 | 64.2 | 65.3 | 77.9 |
| Group 4 (0.01 × Capsule) | 50.2 | 50.4 | 65.6 | 75.5 | 85.0 |
| Group 5 (0.01 × in Feed) | 51.8 | 53.0 | 66.6 | 68.6 | 84.6 |

Of particular interest in the results set forth above is that, in general, the treated turkey poults posted significant weight inreases over the control group for each dilution of the metal proteinate, whether the metal proteinate was forcefed or amended to the diet.

As a further note of significant interest in the foregoing evaluation using turkey poults, deaths of some of the birds was experienced. Death losses which were diagnosed as due to para-color appeared in the control group and at the lower dosage levels of metal proteinate (Groups 1, 3, 4 and 5). The excellent condition of poults in Group 2 suggests a possible beneficial effect of higher levels of the metal proteinate in increasing resistance to para-colon.

Additional benefits to be derived from the discovery that metal deficiencies can first be diagnosed and then corrected through this invention are set forth below in the following examples.

EXAMPLE 4

Ten thousand laying hens were chosen and separated into two groups of five thousand each. The same commerical layer ration was fed both groups. Feathers from representative samples of both groups were assayed to determine the metals profile of the hens. The metals profile thus obtained was compared to a standard profile obtained on the basis of data compiled from assay of feathers from young, healthy, laying hens. Deficiencies were observed and on the basis of this comparison, the commercial feed composition was amended with metal proteinates blended according to Table IV. Controls were fed corresponding amounts of inorganic metals.

TABLE IV

METAL COMPOSITION OR FEED BLEND

| Calcium | 4.5% |
|---|---|
| Magnesium | 4.6% |
| Zinc | .4% |
| Iron | .2% |
| Manganese | .1% |
| Copper | .04% |
| Cobalt | .02% |

The foregoing metal feed blend was thoroughly mixed with the commercial layer ration on the basis of two pounds of metal feed blend per ton of commercial layer ration.

Group 1 received the metals of Table IV as proteinates of each metal. Group 2 received the same amount and ratio of metals blended per ton commercial feed ration as fed Group 1. However, the metals were in the form of inorganic metals. In a 60-day period, the hens of Group 1 which were treated with metal proteinate of the mentioned formulation layed 18,210 more eggs than hens treated with the inorganic metals. Moreover, a very favorable effect on the quality of the eggs was found to result. Eggs from Group 1 required an average of 1.7 pounds more pressure to break the egg shell than eggs from Group 2. Also, the lining of the eggs of Group 1 showed greater tensile strength. An analysis of egg yolk determined that there was 11.14% more zinc, 10.50% more iron and 6.0% more copper in eggs laid by Group 1.

The increase in the number of eggs produced by Group 1 resulted not only from a higher lay rate but also from increased capacity to lay over a longer time span. Table V sets forth the results measured as the percentage of hens laying an average of one egg per day (lay rate) at the peak lay period for the group and six months after the peak. Hens in both groups started laying at 20 weeks of age.

TABLE V

| | Group 1 (Treated) | Group 2 (Control) |
|---|---|---|
| Peak Lay Rate | 85% | 75% |
| 6 Months After Peak | 80% | 64% |

The hens were forced to molt after the sixty-day period. Just prior to molt, assays of the feathers showed that Group 1 averaged 10%–17% higher metal levels than the control Group 2.

EXAMPLE 5

Twenty-five hundred laying hens, which had been in peak lay 3 months, were selected and 25 randomly-selected chicks reproduced by these laying hens were chosen as controls. The average hemoglobin level in gm% of the chicks was 8.7gm%. The hens were then placed on a diet supplemented with the metal proteinate blend of Example 3. Forty-three days later eggs from the treated hens were set and 25 randomly-selected (treated) chicks from those eggs were assayed for hemoglobin. The average hemoglobin of the second group of chicks was 9.4 gms% as compared to 8.7 gms% of the control chicks. Significantly, the death loss in the first seven days of life between the control chicks and the treated chicks decreased from 2.0% to 0.8%.

Accordingly, it was found that supplementing the diet of the laying hens with metal proteinates resulted in improved hemoglobin levels in their offspring and decreased death loss of chicks.

EXAMPLE 6

Five hundred laying hens diagnosed as having avian leucosis were given metal proteinates along with normal feed ingredients. The formulation of the metal proteinates was the same as set forth in Table IV with calcium, magnesium and zinc the predominant ingredients. The yellow appearance of the combs and the wattles which normally attend this disease disappeared within 30 days and the comb and wattle returned to the normal red color. Also, the birds took on a healthy appearance and the death loss became negligible. Egg production and the quality of the egg shell returned to the normal range within this thirty-day period while egg breakage in the nests was decreased 97%.

EXAMPLE 7

Five races of fingerling cut throat trout, each race having approximately fifty thousand fish, were each given a feed ration with an addition of one-half percent per ton of a metal proteinate formulation (see Table IV). The five races of fish were compared with a race of control fish given the same feed ration without the metal proteinate addition. Samples of the fish in each race were weighed every two weeks for approximately one year. It was discovered that the feed conversion, i.e., the amount of food required to produce one pound of meat, was much higher in the fish fed with rations having the metal proteinate addition. The treated fish consumed an average of 1.2 pounds of feed per pound of weight gained while the control trout consumed an average of 4.2 pounds of feed per pound of weight gained.

EXAMPLE 8

Anemia in baby pigs due to iron deficiency has historically been a problem when sows and their offspring are confined without access to the soil or pasture. The baby pigs are particularly susceptible to this type of anemia because of their high rate of growth, low body reserves of iron at birth, and low iron levels in sow's milk. A normal growth rate for baby pigs means an increase in body weight of four to five times their birth weight at the end of only three weeks. A growth rate of this magnitude requires the retention of about 7 mgs. of iron per day. However, sow's milk supplies only about 1 mg. per day and baby pigs consume little feed other than sow milk for the first three or four weeks. Accordingly, the need for an iron dietary supplement is readily apparent.

Inorganic iron supplements fed to the sow both before and after farrowing has proven ineffective in either raising the iron content of the sow's milk significantly or increasing the iron levels of the baby pigs at birth. Treating the baby pigs is routinely accomplished either by (a) oral administration of 400 to 500 mgs. inorganic iron as tablets or solutions within four days of birth and again at two weeks, or (b) at least two injections of 100 to 200 mgs. iron-complex solution during the early growth period. The foregoing has proven inadequate since even frequent treatment by these steps is insufficient to allow the piglets to achieve maximum growth. This shortcoming is further compounded by the handling requirements of large numbers of animals which renders the procedure impractical. Accordingly, it is most desirable to assay tissue (e.g. blood) from the animal and amend the diet of the sow with appropriate metals and in sufficient amounts to enable the sow to pass the metals to the piglets through the sow's milk.

After suitable analysis, the following formulation of Table VI was prepared as a dietary supplement for sows. The metals were formulated as proteinates.

TABLE VI

| ASSAY OF METAL PROTEINATE FOR SWINE | |
|---|---|
| Metal | Percent Composition |
| Mg | 6.80% |
| Fe | 1.86 |
| Zn | 1.26 |
| Cu | 0.05 |
| Co | 0.0024 |

The foregoing formulation of Table VI was fed to one group of sows at a rate of five pounds per ton of feed and the same formulation of metals as inorganic metals was fed to a second group of sows also at a rate of five pounds per ton of feed. This second group of sows served as a control. A random sample of both the treated and control feed rations analyzed for metal content showed 14 mg. iron/100 grams.

Blood hemoglobin levels were determined initially (thirty days prior to anticipated farrowing) and continued until the piglets were weaned at about sixty days of age. Piglet weights and blood hemoglobin levels were determined at birth and upon weaning. The results of hemoglobin determinations and piglet weights are set forth in Tables VII and VIII below:

TABLE VII

| | HEMOGLOBIN (Hb) LEVELS (gm/100 ml) | | | |
|---|---|---|---|---|
| | Control | | Treated | |
| Group | Hb Range | Average | Hb Range | Average |
| Sows Initially | 12–15 | 13.5 | 12–14 | 13.5 |
| At farrowing | 12–14 | 13.3 | 13–15 | 14.3 |
| Litters | | | | |
| At birth | 7.5–9.8 | 9.0 | 9.6–12.0 | 11.0 |
| At weaning | 10.7–12.0 | 11.7* | 11.9–12.8 | 12.2 |

*some piglets required iron injections

TABLE VIII

| | LITTER WEIGHTS | |
|---|---|---|
| | (Average in Pounds) | |
| | Control | Treated |
| Birth | 3.60 lbs. | 3.53 lbs. |
| Weaning | 37.25 lbs. | 39.25 lbs. |
| Gain | 33.00 lbs. | 35.65 lbs. |

It should be particularly emphasized that in the foregoing example some of the control piglets required iron-complex injections to prevent loss of the piglets and, therefore, the hemoglobin level for the control piglets may be artificially high. Even with injections given to the control piglets, the piglets which nursed on treated sows had higher hemoglobin levels and heavier weights at weaning.

From the foregoing, it is clear that surprisingly beneficial effects result from making essential metals available to animals in a biologically acceptable form. With these essential metals readily available to the animals, the animal is no longer required to synthesize its own metal proteinate from inorganic metals and thus individual differences in biological capability of animals are no longer responsible for an inadequate nutritional level of metals.

Furthermore, a determination of the metal level in the tissue of a healthy animal to establish a standard and comparison of the metal level of a selected animal with that standard enables one to suitably prescribe a corrective dietary supplement.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:

1. A method of raising the levels of essential bivalent metals in the tissues of animals which comprises administering to said animal an effective amount of exogenously synthesized metabolically assimilable metal proteinates, said proteinates being in the form of chelates of said metals with one or more protein hydrolysates selected from the group consisting of polypeptides, peptides and amino acids wherein said proteinates are formed by dissolving salts of said metals in an aqueous solution containing the protein hydrolysates and adding sufficient base to raise the ph to a value between about 7.5 and 10 to precipitate said metal proteinates.

2. A method according to claim 1 wherein the effective amount of each metal proteinate is in a dosage effective to correct an existing metal deficiency in the animal during the period over which the metal proteinate is administered.

3. A method according to claim 2 wherein the metal proteinate is an iron proteinate.

4. A method according to claim 2 wherein the metals in the metal proteinates are selected from the group consisting of calcium, magnesium, zinc, iron, manganese, copper and cobalt.

5. A method according to claim 4 wherein the metal proteinates are administered in the form of a dietary supplement.

6. A method according to claim 5 wherein the existing metal deficiency is determined by analysis of the tissues of the animal to which the metal proteinates are to be administered.

7. A method according to claim 6 wherein the tissues analyzed are selected from the group consisting of hair, feathers, hoofs, horns, skin, flesh and blood.

8. A method for treating anemia in piglets which comprises administering an effective dosage of a metal proteinate according to claim 1 to a farrowing sow during the latter stages of pregnancy and during lactation.

9. A method according to claim 8 wherein the metal protein is an iron proteinate in admixture with other metal proteinates selected from the group consisting of magnesium, zinc, copper, and cobalt proteinates.

10. A method according to claim 8 wherein the metal proteinate is an iron proteinate.

11. A composition for raising the levels of essential bivalent metals in tissues of animals comprising an animal feed and an effective mixture of exogenously synthesized metabolically assimilable metal proteinates, said metal proteinates being in the form of chelates of said metals with one or more protein hydrolysates selected from the group consisting of polypeptides, peptides, and amino acids wherein said proteinates are formed by dissolving salts of said metals in an aqueous solution containing the protein hydrolysates and adding sufficient base to raise the ph to a value between about 7.5 and 10 to precipitate said metal proteinates.

12. A composition according to claim 11 wherein the metals are selected from the group consisting of calcium, magnesium, zinc, iron, manganese, copper and cobalt.

13. A composition for raising the levels of essential bivalent metals in tissues of animals comprising a lactose diluent and an effective amount of exogenously synthesized metabolically assimilable metal proteinates, said meal proteinates being in the form of chelates of said metals with one or more protein hydrolysates selected from the group consisting of polypeptides, peptides and amino acids wherein said proteinates are formed by dissolving salts of said metals in an aqeuous solution containing the protein hydrolysates and adding sufficient base to raise the ph to a value between about 7.5 and 10 to precipitate said metal proteinates.

14. A composition for raising the levels of essential bivalent metals in tissues of animals comprising in addition to a feed a dietary supplement containing an effective amount of a mixture of exogenously synthesized metabolically assimilable metal proteinates, said metal proteinates being in the form of chelates of said metals with one or more protein hydrolysates selected from the group consisting of polypeptides, peptides and amino acids wherein said proteinates are formed by dissolving salts of said metals in an aqueous solution containing the protein hydrolysates and adding sufficient base to raise the ph to a value between about 7.5 and 10 to precipitate said metal proteinates.

* * * * *